US011541357B2

(12) United States Patent
Pflanz et al.

(10) Patent No.: US 11,541,357 B2
(45) Date of Patent: Jan. 3, 2023

(54) FILTER MODULE AND METHOD FOR DETECTING MICROORGANISMS

(71) Applicant: Sartorius Stedim Biotech GmbH, Goettingen (DE)

(72) Inventors: Karl Pflanz, Goettingen (DE); Roland Leetsch, Bovenden (DE); Sebastian Pruehl, Wehnde (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 464 days.

(21) Appl. No.: 16/867,725

(22) Filed: May 6, 2020

(65) Prior Publication Data

US 2020/0261853 A1 Aug. 20, 2020

Related U.S. Application Data

(63) Continuation of application No. PCT/EP2018/078905, filed on Oct. 22, 2018.

(30) Foreign Application Priority Data

Nov. 6, 2017 (DE) .......................... 102017125881.7

(51) Int. Cl.
*B01D 63/08* (2006.01)
*B01L 3/00* (2006.01)
(Continued)

(52) U.S. Cl.
CPC .......... *B01D 63/087* (2013.01); *B01L 3/5635* (2013.01); *C12Q 1/04* (2013.01);
(Continued)

(58) Field of Classification Search
CPC ........ B01D 2311/08; B01D 2311/2688; B01D 2313/13; B01D 2313/18; B01D 2313/50;
(Continued)

(56) References Cited

U.S. PATENT DOCUMENTS 4,036,698 A 7/1977 Bush et al.
5,375,477 A 12/1994 Neill et al.
(Continued)

FOREIGN PATENT DOCUMENTS

CN 102686793 A 9/2012
CN 105874084 A 8/2016
(Continued)

OTHER PUBLICATIONS

International Search Report, PCT/EP2018/078905, dated Mar. 4, 2019, 5 pages.

*Primary Examiner* — Jennifer Wecker
(74) *Attorney, Agent, or Firm* — Edell, Shapiro & Finnan, LLC

(57) ABSTRACT

A filter module (10) has a housing (12) which is subdivided by a membrane filter (14) into an inlet chamber (16), which is connected to an inlet connecting piece (22) arranged rigidly on the housing (12), and an outlet chamber (18), which has a filtrate outlet (20). The inlet connecting piece has two connectors, specifically a first connector (26) and a second connector (28), which connect selectively and fluidically to the inlet chamber with a 3-way valve (24) integrated into the inlet connecting piece. The valve has a first entry, which is connected to the first connector, a second entry, which is connected to the second connector, and an exit, which is connected to the inlet chamber. The first connector is configured as an adapter for outwardly sealed coupling of a culture medium bottle (30), which coupling permits a gravity-driven exchange of liquid with the first entry of the valve.

13 Claims, 5 Drawing Sheets

(51) Int. Cl.
*C12Q 1/04* (2006.01)
*G01N 1/40* (2006.01)

(52) U.S. Cl.
CPC ....... *G01N 1/4077* (2013.01); *B01D 2313/13* (2013.01); *B01D 2313/18* (2013.01); *B01D 2313/50* (2013.01); *B01D 2313/90* (2013.01); *B01D 2315/08* (2013.01); *B01L 2300/0681* (2013.01); *B01L 2400/065* (2013.01); *G01N 2001/4088* (2013.01)

(58) Field of Classification Search
CPC ............ B01D 2313/90; B01D 2315/08; B01D 63/087; B01L 2300/0672; B01L 2300/0681; B01L 2400/065; B01L 3/5635; C12Q 1/04; G01N 1/4077; G01N 2001/4088
See application file for complete search history.

(56) References Cited

U.S. PATENT DOCUMENTS

| | | |
|---|---|---|
| 6,294,090 B1 | 9/2001 | Nussbaumer et al. |
| 2012/0238007 A1 | 9/2012 | Wilson et al. |
| 2014/0356874 A1 | 12/2014 | Bearinger et al. |
| 2017/0002395 A1 | 1/2017 | Baumstummler et al. |

FOREIGN PATENT DOCUMENTS

| | | |
|---|---|---|
| CN | 106475162 A | 3/2017 |
| DE | 102014007848 A1 | 11/2015 |
| EP | 1395646 B1 | 7/2010 |
| EP | 2365237 A1 | 9/2011 |
| EP | 3124595 A1 | 2/2017 |
| WO | 2013159117 A1 | 10/2013 |
| WO | 2015061480 A1 | 4/2015 |
| WO | 2017071795 A1 | 5/2017 |

FILTER MODULE AND METHOD FOR DETECTING MICROORGANISMS

CROSS REFERENCE TO RELATED APPLICATIONS

This is a Continuation of International Application PCT/EP2018/078905 which has an international filing date of Oct. 22, 2018, and the disclosure of which is incorporated in its entirety into the present Continuation by reference. This Continuation also claims foreign priority under 35 U.S.C. § 119(a)-(d) to and also incorporates by reference, in its entirety, German Patent Application DE 10 2017 125 881.7 filed on Nov. 6, 2017.

FIELD OF THE INVENTION

The invention relates to a filter module comprising a housing which is subdivided by a membrane filter into an inlet chamber, which is connected to an inlet connecting piece arranged rigidly on the housing, and an outlet chamber, which has a filtrate outlet.

The invention furthermore relates to a method for detecting microorganisms in a test liquid using such a filter module.

Generic filter modules and detection methods are known from U.S. Pat. No. 4,036,698.

BACKGROUND

In many sectors, for example in the food, pharmaceutical and biotechnological industries, the sterility of liquids used or produced is of fundamental importance. Correspondingly great effort is required for detecting microorganisms possibly contained in such liquids. The following method has long been established for this purpose: The liquid to be tested, referred to as test liquid here, is pumped through a membrane filter whose properties, in particular the pore size thereof, are configured such that the microorganisms in question cannot pass through and, when the liquid flows through, are deposited on the surface of said membrane filter. After a representative portion of the test liquid has been filtered, so that a representative portion of the microorganisms possibly contained has accumulated on the filter, the filter is wetted with a suitable culture medium and incubated under growth-promoting conditions. In this case, the microorganisms which have possibly accumulated on the filter surface multiply to an extent at which they can be detected with suitable detection means. If standardized process steps are followed, highly reproducible and comparable results can thus be obtained.

In order to avoid contamination-prone removal and transfer of the filter from the filter module into an incubation container, the aforementioned document, which constitutes the generic type, proposes the dual use of the filter module as both a filter holder and an incubation vessel. In the region of its inlet chamber, the housing of the known filter module has an inlet connecting piece for liquid, and a venting connecting piece which is provided with a sterile filter. In its outlet chamber on the other side of the membrane filter subdividing the housing, provision is made of a filtrate outlet formed as an outlet connecting piece. In the first step, test liquid is pumped via a tube connection through the inlet connecting piece into the inlet chamber, through the membrane filter into the outlet chamber, and through the outlet connecting piece into a collecting container. Then, that is to say afterwards or after one or more optional intermediate cleaning and/or flushing steps, the outlet connecting piece is closed off. The tube connection to the inlet connecting piece is eliminated and replaced by a tube connection to a culture medium bottle. A vacuum pump is connected to the venting connecting piece. By way of said vacuum pump, culture medium is then sucked from the culture medium bottle into the inlet chamber such that the membrane filter is wetted with culture medium. After the tube and pump connection means have been pulled off, the inlet and venting connecting pieces are closed off and the incubation step, in which the inlet chamber serves an incubation container, follows. The incubation result is checked through the transparent housing wall in the form of a color and/or turbidity measurement. The cited document suggests carrying out the filtration in a parallel manner with two filter modules, the inlet chambers of which are filled with different culture media, in particular culture media for aerobic and for anaerobic microorganisms, prior to the incubation step.

A similar principle is known from US 2017/0002395 A1, wherein however, the filter module is provided with a rotating mechanism by way of which the tube connection to the inlet connecting piece can be broken more quickly and easily and the inlet connecting piece can be closed off. Beside the complicated and error- and contamination-prone handling, which is associated with the change in the tube connections, a disadvantage of the systems mentioned is also the long incubation time, often of several days, that is required until the formation of a reaction which is measurable in the manner described above.

Incubation containers having integrated microorganism activity sensors are known from US 2012/0238007 A1. On the market, containers of said type are closed off in a sterile manner and are only in part available filled with a culture medium which is matched to the microorganisms specifically to be detected. The test liquid which is to be checked for the presence of microorganisms is injected through a septum closure into the culture medium bottle, which is then used as an incubation container. The activity of the microorganisms leads to a change in an externally detectable property of the integrated sensor, for example to a change in colour. However, said method requires a relatively high content of microorganisms in the test liquid, of which only small volumes can be tested using this method. This approach is not suitable for detecting very low contaminations of nominally sterile test liquids or for testing large volumes.

SUMMARY

It is an object of the present invention to further develop a generic filter module and a generic detection method in a manner that provides a filter module and a detection method that result in simplified and less error- and contamination-prone handling.

According to one formulation, this object is achieved with a filter module comprising: a housing which is subdivided by a membrane filter into an inlet chamber, which is connected to an inlet connecting piece arranged rigidly on the housing, and an outlet chamber, which has a filtrate outlet, and a 3-way valve integrated into the inlet connection piece, wherein the inlet connecting piece has two connectors, specifically a first connector and a second connector, which are configured to selectively connect fluidically to the inlet chamber with the 3-way valve, wherein the 3-way valve comprises a first entry, which is connected to the first connector, a second entry, which is connected to the second connector, and an exit, which is connected to the inlet chamber, and wherein the first connector is configured as an adapter for outwardly sealed coupling of a culture medium bottle, which coupling permits a gravity-driven exchange of liquid with the first entry of the 3-way valve.

According to a further formulation, this object is achieved by a method for detecting microorganisms in a test liquid, comprising:

a) providing a filter module of said type, wherein only its second connector, by way of a corresponding switching position of the 3-way valve, is connected to the inlet chamber, b) coupling on a culture medium bottle with the adapter, wherein the culture medium bottle contains culture medium and an integrated microorganism activity sensor, c) connecting the second connector to a test liquid reservoir, d) pumping test liquid from the test liquid reservoir through the filter module, e) switching the 3-way valve such that only the first connector thereof is connected to the inlet chamber, f) orienting the filter module and the coupled-on culture medium bottle such that both the membrane filter and the microorganism activity sensor are wetted by the culture medium, g) monitoring the microorganism activity sensor.

Preferred embodiments are the subject matter of the dependent patent claims.

The invention takes up the basically known idea of dual usage of the inlet chamber of the filter module as such and as an incubation container. Taking this as a starting point, the invention firstly simplifies the necessary change of the tube connection, to a test liquid reservoir on the one hand and to a culture medium reservoir on the other hand, by the provision of a valve unit integrated into the filter module, in particular into the inlet connecting piece thereof. In this way, a manual changeover with respect to the plugging of tube connections is rendered superfluous and replaced by an easily automatable switching process of a 3-way valve, which switches the connection of the inlet chamber to the test liquid reservoir (via the second connector) to a connection of the inlet chamber to the culture medium bottle (via the first connector). The expression "3-way valve" is to be understood here in a broad sense and means only that said valve has at least three ports (first entry, second entry, exit). These must be connectable to one another in at least the aforementioned two positions, that is to say such that the ports are at least in each case individually able to be connected fluidically to the inlet chamber. Preferably, a 3/2-way valve having exactly three ports and exactly two switching positions is used. However, if a more complex valve is required in individual cases, for example because use is to be made of test liquid from multiple sources, this is also possible within the scope of the invention.

In this respect, in one refinement of the invention, it may be provided for example that the connectors, in addition, are jointly able to be to connected fluidically, via different flow paths, to the inlet chamber. In other words, in this refinement of the invention, there is realized an additional switching position in which the first connector is connected to the inlet chamber via a first flow path and in which the second connector is connected to the inlet chamber via a second flow path, which differs from the first flow path. In the—preferred—case of the configuration of the valve as a slide valve, such a switching position may be configured for example as an additional slide position of the valve piston. Alternatively, it is also possible for a particular rotational position of the valve piston to be provided.

The refinement mentioned of the device according to the invention permits a particularly advantageous refinement of the method according to the invention. In the case thereof, between the aforementioned steps d and e, the following additional steps are provided:

d1) switching the 3-way valve such that the first connector and the second connector thereof are jointly connected, via different flow paths, to the inlet chamber, d2) pumping culture medium from an external culture medium reservoir, connected to the second connector, through the inlet chamber into the coupled-on culture medium bottle.

As an alternative to step d2), the following step may also be provided:

d2) pumping culture medium from the coupled-on culture medium bottle into a waste reservoir connected to the second connector.

The expression "waste reservoir" is to be interpreted here in a broad sense. In particular, there is no need for a separate vessel dedicated exclusively to the purpose of storing waste. Suitability for receiving a small quantity of culture medium exiting from the second connector is sufficient. In particular, use may be made of a connection tube arranged anyway between the test liquid reservoir and the second connector.

This is because it has been found in practice that the growth into the culture medium bottle to the microorganism activity sensor of the microorganisms accumulated on the membrane filter can be yet further improved in this way. If, just prior to the final switching of the valve into its position connecting only the first connector, that is to say the culture medium bottle, to the inlet chamber, a small quantity of culture medium is pumped through the inlet chamber (and through the first connector) into the culture medium bottle or in reverse from the culture medium bottle through the inlet chamber (and through the first connector), the entire path from the membrane filter to the microorganism activity sensor is in this way already filled with culture medium prior to the incubation. Any dead volume is eliminated, and is flooded with the growth-promoting culture medium. The path through the valve into the culture medium bottle and to the microorganism activity sensor is consequently facilitated for the microorganisms which, during the incubation, grow from the membrane filter.

A further advantage of this additional valve setting is the possibility of carrying out an equalization of pressure between the connected culture medium bottle and the surroundings represented by the test liquid reservoir. Commercially available culture medium bottles with microorganism activity sensor are normally subjected to negative pressure. This results from their typical use in blood sampling. In the context of their use according to the invention, however, a pressure difference with respect to the surroundings is rather disadvantageous. The temporary short circuit between the culture medium bottle and the surroundings—whether it be an additional culture medium reservoir or a waste reservoir—can overcome this disadvantage. In contrast, the negative pressure in the culture medium bottle can even be used advantageously as a drive for the pumping of culture medium from the external culture medium reservoir into the culture medium bottle.

A further special feature of the invention is the specific configuration of the first connector, provided for the coupling to the culture medium bottle, of the inlet connecting piece. Said first connector is configured as an adapter for direct connection to a bottle neck of a culture medium bottle. After being coupled via the adapter, the inlet connecting piece and the culture medium bottle form a rigid unit which can oriented arbitrarily. In particular, this rigid coupling makes it possible for the culture medium bottle and the filter module coupled thereon to be tilted such that the culture medium flows from the bottle mouth to the 3-way valve and, from there, provided said valve is correctly switched, onward into the inlet chamber of the filter module and onward to the membrane filter. As a result of the direct coupling, the path is so short here that, possibly with the assistance of a continuous pivoting movement, the membrane filter and a microorganism activity sensor integrated in the culture medium bottle are constantly wetted and in liquid-exchanging contact with one another. However, this is only possible if, as provided according to the invention, the adapter creates a sufficiently large connection between the culture medium bottle and the first entry of the 3-way valve, such that the culture medium can flow back and forth between the microorganism activity sensor and the membrane filter in a gravity-driven manner, that is to say without application of an external positive or negative pressure (for example with a pump).

A filter module configured according to the invention in this manner allows the detection method, which is known and well-established in principle, to be implemented with few, simple steps, which exclude practically any errors and are also easily automatable. The steps to be carried out are specified above in the context of the detection method according to the invention, wherein the specified listing does not imply a requisite sequence for the steps. In particular, the step of coupling on the culture medium bottle (step b) may be realized at any desired point in time prior to the switching of the 3-way valve (step e). Also feasible and covered by the wording of the claim is the possibility of distributing, as a sterile unit, culture medium bottles with filter module already coupled on, that is to say essentially carrying out step b before step a.

In a preferred embodiment of the filter module according to the invention, the adapter has a central cannula and a collar which engages coaxially around the latter. The inner diameter of the collar has to be matched to the outer diameter of the bottle neck or of the bottle mouth of the culture medium bottle. In this way, said adapter ensures a rigid, in particular flexurally rigid, form-fitting connection between the culture medium bottle and the filter module, which permits in particular the horizontal storage of the culture medium bottle with coupled-on filter module. The cannula, on the other hand, serves for the liquid-exchanging coupling between the culture medium bottle and the inlet chamber of the filter module. As explained above, it has to have an inner diameter which permits a purely gravity-driven exchange of liquid. For a person skilled in the art, it would be easy to select a suitable cannula diameter, with the cannula length and the viscosity of the culture medium taken into account. Preferably, the cannula diameter is between 1 mm and 5 mm. The configuration of the liquid connection as a cannula is particularly expedient in view of the normal configuration of the closures of culture medium bottles as a septum closure.

In order to realize not only flexural rigidity of the coupling but also axial securing, by way of which inadvertent axial pulling-off of the filter module from the culture medium bottle can be prevented, various measures may be implemented.

In a first preferred refinement of the invention, it is provided that the collar is subdivided into at least two collar segments, which are adjacent to one another in a circumferential direction and which are elastically pivotable relative to one another about in each case one tangential pivot axis. Here, the collar preferably has radially inwardly projecting detent projections, in particular at its collar boundary. This gives rise to a detent mechanism which is suitable in particular for coupling on a culture medium bottle having a bottle mouth which is thickened in relation to the bottle neck. When pushed onto the culture medium bottle, the collar segments are spread relative to one another. However, as soon as the detent projections have been pushed over the bottle mouth, they snap, driven by the elasticity of the collar segments, radially inward and engage behind the boundary of the thickened bottle mouth. In this way, the axial securing mentioned is realized.

The embodiment mentioned of a segmented collar has particular advantages with regard to facilitated demolding in an injection molding tool for the production thereof. With sufficient material elasticity, however, a closed collar, in particular having an encircling detent boundary, is also an option.

If the detent projections or the detent boundary, as preferably provided, have/has a rear bevel, it is possible, in combination with an elastic seal bearing against the bottle boundary, to generate a permanent axial force by which the filter module and the culture medium bottle are drawn toward one another. Moreover, it is possible in this way to compensate for manufacturing tolerances and to design the overall system without play.

In a likewise preferred, alternative refinement of the invention, it is provided that the collar has an internal thread. Such an adapter is suitable in particular for coupling on culture medium bottles having a corresponding external thread.

Particularly advantageous in practice, albeit technically highly complex, is one refinement of the invention in which two positions, specifically an active position and a passive position, are provided for the coupling of the adapter to the culture medium bottle. In the passive position, the adapter and the culture medium bottle are already connected mechanically, but are not yet connected fluidically. In the active position, the adapter and the culture medium bottle are additionally also connected fluidically.

Several variants are available for the configuration of this embodiment. In this respect, provision may be made of a cannula which is mounted movably and which, upon the transition from the passive position into the active position, is folded, and/or axially displaced, such that it pierces a septum closure of the culture medium bottle. Preferably, this movement of the cannula is coupled with the switching of the 3-way valve. In one irreversibly switchable variant of the valve, which is described in more detail below, the cannula may be used as a blocking element.

A configuration of the above-explained detent collar with two detent positions, which are realized for example by two axially spaced-apart detent boundaries (which are encircling or composed of individual projections), the first one of which is associated with the passive position and the second one of which is associated with the active position, is also feasible.

In principle, the 3-way valve may be designed in any desired manner; particularly preferably, as already mentioned further above, said 3-way valve is configured as a slide valve. In contrast to a ball valve, for example, a slide valve is a great deal flatter, so that the distance between the inlet chamber of the filter module and the culture medium bottle is minimized. Such a particularly space-saving configuration is also advantageous with regard to the space available in commercially available incubation cabinets.

Moreover, the exchange of liquid between the filter module and the culture medium bottle is all the better the shorter the distance to be spanned is.

It is preferably provided that the 3-way valve is able to be switched irreversibly into its switching position which (exclusively) connects the first connector to the inlet chamber from its switching position which (at least also) connects the second connector to the inlet chamber. In the case of a slide valve, this may be realized for example with a unidirectional detent which let the valve piston engage with detent action at the valve housing as soon as this reaches the second switching position mentioned above. This can reliably prevent a situation in which the user, after a switching of the valve in the way intended, inadvertently performs a switching-back action and thus causes loss of sterility during the incubation or an interruption to the connection between the culture medium bottle and the membrane filter. In the case mentioned further above of a movably mounted cannula, this may also be used for blocking the valve piston.

The displaceably mounted valve piston of the slide valve may be provided with an uncoupling mechanism for the second connector, which, upon switching of the valve, simultaneously breaks the tube connection to the second connector.

Expediently, the first connector of the inlet connecting piece is oriented perpendicular to the membrane filter, and the second connector of the inlet connecting piece is oriented parallel to the membrane filter. This has the result that, in the coupled-on state, the culture medium bottle and the membrane filter are oriented so as to be coaxial with one another (albeit axially adjacent to one another). Here, the filter module may be considered to be, as it were, an extension of the culture medium bottle. This configuration facilitates the classic horizontal positioning of the culture medium bottle in the incubation cabinet and/or on a rocking platform, so that the above-described wetting of membrane filter and microorganism activity sensor is ensured.

Further features and advantages of the invention will emerge from the following specific description and the drawings.

DETAILED DESCRIPTION

Identical reference signs in the Figures indicate identical or analogous elements.

Figure 1:
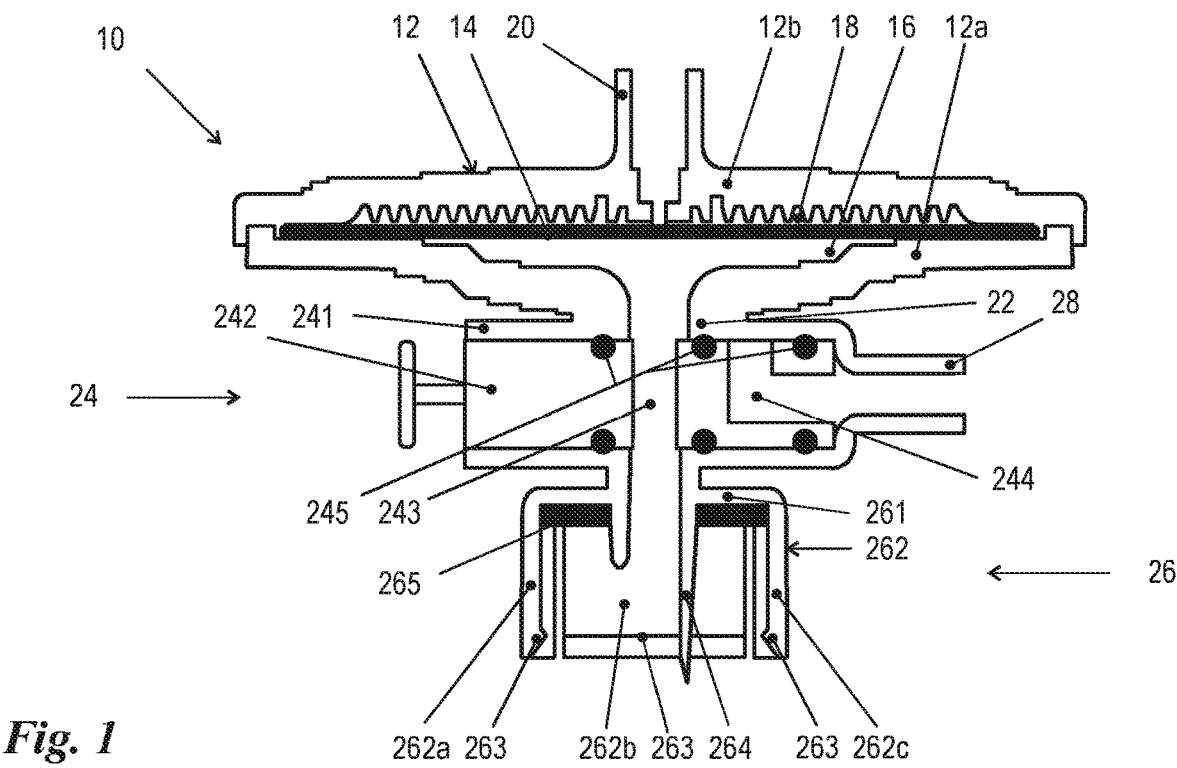
FIG. 1 shows a sectional illustration of a filter module according to the invention in a first valve position.

FIG. 1 shows a filter module 10 according to the invention in a first valve position. The filter module 10 comprises a housing 12 which is subdivided into two chambers by a membrane filter 14 which is clamped (and/or glued, welded, etc.) in a liquid-tight manner between two housing halves 12 a, 12 b. The inlet chamber 16 extends between the membrane filter 14 and the lower housing half 12 a. The outlet chamber 18 extends between the membrane filter 14 and the upper housing half 12 b and opens into a central outlet connecting piece 20 which serves as a filtrate outlet.

Figure 2:
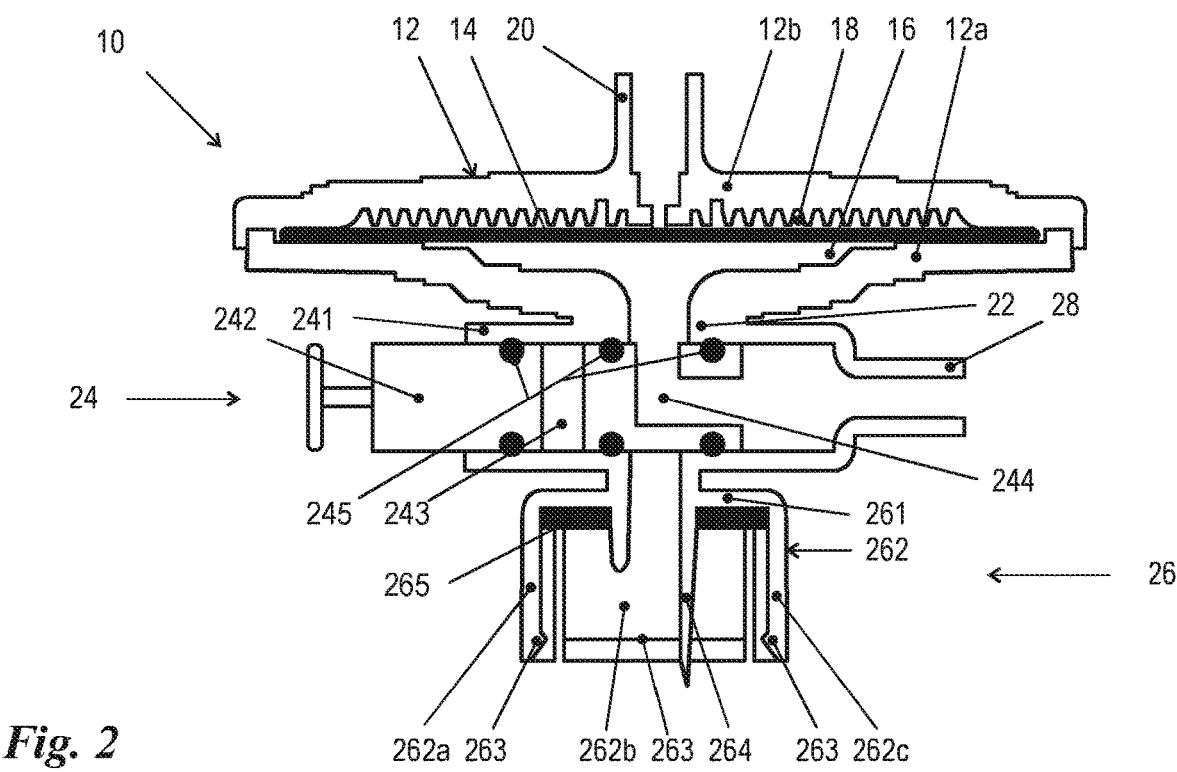
FIG. 2 shows a sectional illustration of a filter module according to the invention in a second valve position.

The inlet chamber 16 opens into a central inlet connecting piece 22 which has an integrated slide valve 24 via which said inlet connecting piece is split into two connectors, specifically a first connector 26 and a second connector 28. The slide valve 24 is configured as a 3/2-way valve, with which the inlet chamber 16—according to valve position—is selectively able to be connected either to the first connector 26 of the inlet connecting piece 22 (FIG. 1) or to the second connector 28 of the inlet connecting piece 22 (FIG. 2). In the illustrated embodiment, the slide valve 24 comprises a valve housing 241 which extends parallel to the plane of extent of the membrane filter 14 and in which a valve piston 242 is slidably mounted. The valve piston 242 is passed through by a first valve channel 243, which passes through the valve piston 242 transversely, and by a second valve channel 244, which is adjacent to said first valve channel and is of angled form and bends from an orientation transverse to the sliding direction off into an orientation parallel to the sliding direction. The inlets and outlets of the channels 243, 244 are sealed off by seals 245 which are fixed on the valve piston 242.

In the illustrated embodiment, the first connector 26 of the inlet connecting piece 22 is configured as a cap constructed from a cover 261 and a collar 262, wherein the collar is subdivided into individual collar segments 262 a, 262b, 262c, which are elastically pivotable about their respective connecting line with respect to the cover 261. Typically, no structural articulation is provided for this purpose, but rather the pivotability of the collar segments 262 a, b, c results from the material and dimensional elasticity of the collar 262. In the region of their lower boundary in FIG. 1, the collar segments 262 a, b, c each have a radially inwardly directed detent projection 263 with front and rear run-on bevels, the function of which will be discussed in more detail further below.

The cover 261 is in the form of a sharp cannula 264 in the region of its central opening and bears a flat seal 265 in the annular region around the cannula 264. For cost reasons, this may preferably be injection moulded onto the cover with the same material during a plastic injection molding process. Gluing-in or injection molding of a cannula made from a different material, in particular a metal cannula, which can be sharpened at its free end, is however also feasible.

FIG. 2 shows the same filter module 10 as FIG. 1, albeit in a second valve position of the slide valve 24, in which valve position the second connector 28 is connected to the inlet chamber 16.

Figure 3:
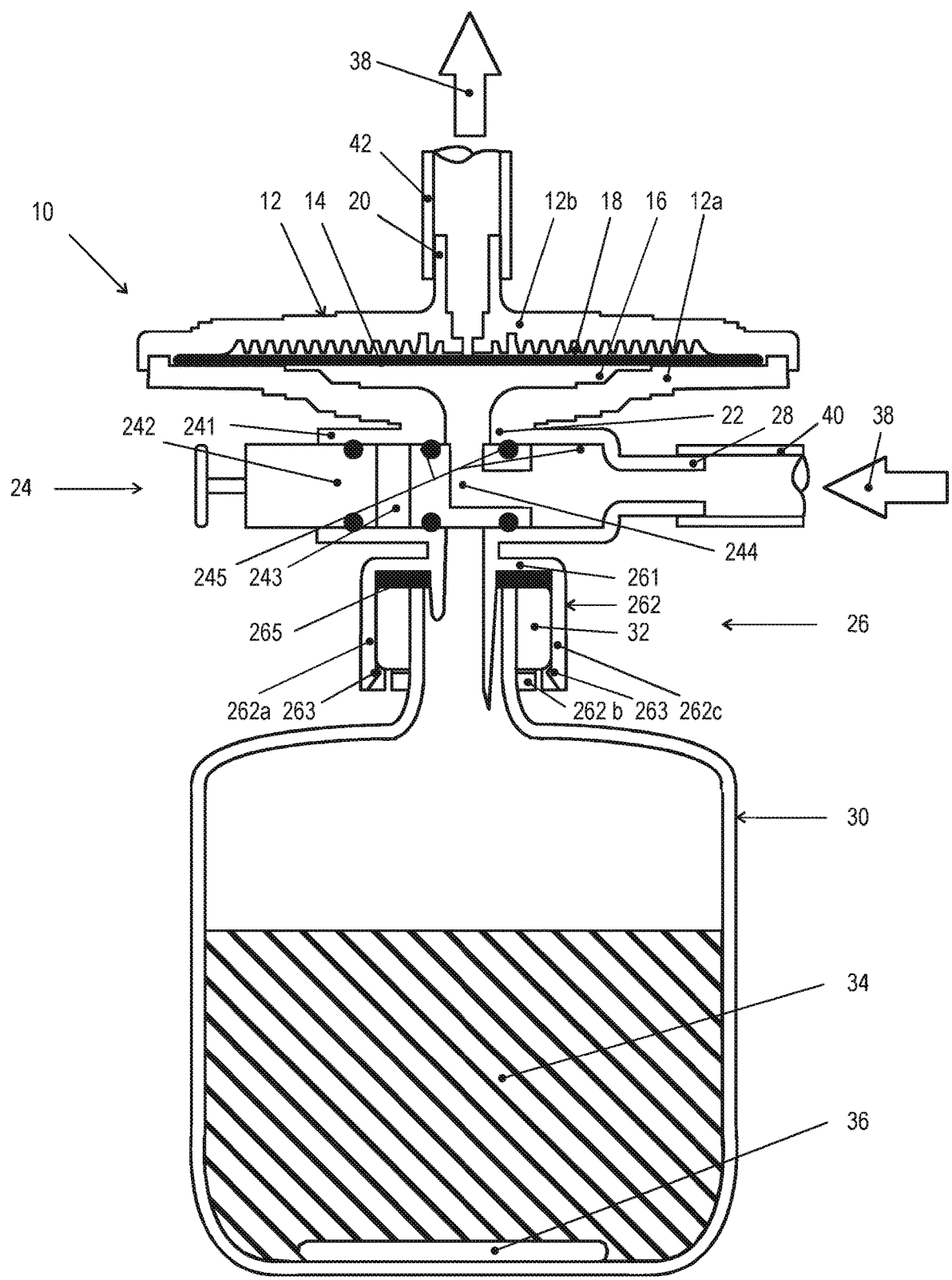
FIG. 3 shows the filter module in FIGS. 1 and 2 in a position of coupling with a culture medium bottle during the filtering step of the detection method according to the invention.

FIG. 3 shows the filter module 10 in FIGS. 1 and 2 in a position of coupling in a culture medium bottle 30. In the region of its bottle neck, the culture medium bottle 30 has a mouth thickening 32. In the uncoupled state, the mouth itself is closed off by a septum (not visible in FIG. 3). When the culture medium bottle 30 is coupled to the first connector 26, the cannula 264 pierces the septum and thus establishes a connection to the slide valve 24. When the cap of the first connector 26 is pushed on axially, the collar segments 262 a, b, c are spread via their front run-on surfaces by the mouth thickening 32. Upon further advancement, the detent projections 263 then snap in behind the mouth thickening 32 and form an axial fastener against inadvertent pulling-off of the filter module 10 from the culture medium bottle 30. At the same time, the bottle mouth is pulled against the flat seal 265 by the rear run-on bevels such that the coupling between the filter module 10 and the culture medium bottle 30 is permanently subjected to force and reliably liquid-tight.

The culture medium bottle 30 is partly filled with a medium 34. It has a microorganism activity sensor 36 on its base. Said sensor may for example be an element which undergoes a change of color upon contact with carbon dioxide (produced by microorganisms) in the culture solution. It is of course also possible for other types of microorganism activity sensors to be used. What is important for practical purposes is the ability to monitor or read the sensor 36 from outside the culture medium bottle 30, for example optically through the base of the bottle.

As already indicated in the general description, the specific point in time at which the above-described coupling between the filter module 10 and the culture medium bottle 30 is realized in a detection method according to the invention is largely arbitrary. In the embodiment described below, which is considered to be particularly advantageous, said coupling is realized prior to the filtering step, which filtering step is indicated in FIG. 3 by means of the flow arrows 38. Test liquid is pumped via a tube connection 40 through the second connector 28 of the inlet connecting piece 22 into the inlet chamber 16, through the membrane filter 14 into the outlet chamber 18, and via the outlet connecting piece 20 and a tube connection 42 connected thereto into a collecting container (not illustrated). During this step, the slide valve 24 must of course be in its second slide position. During this filtering step, any microorganisms present in the test liquid accumulate on the membrane filter 14 on the inlet chamber side.

Figure 4:
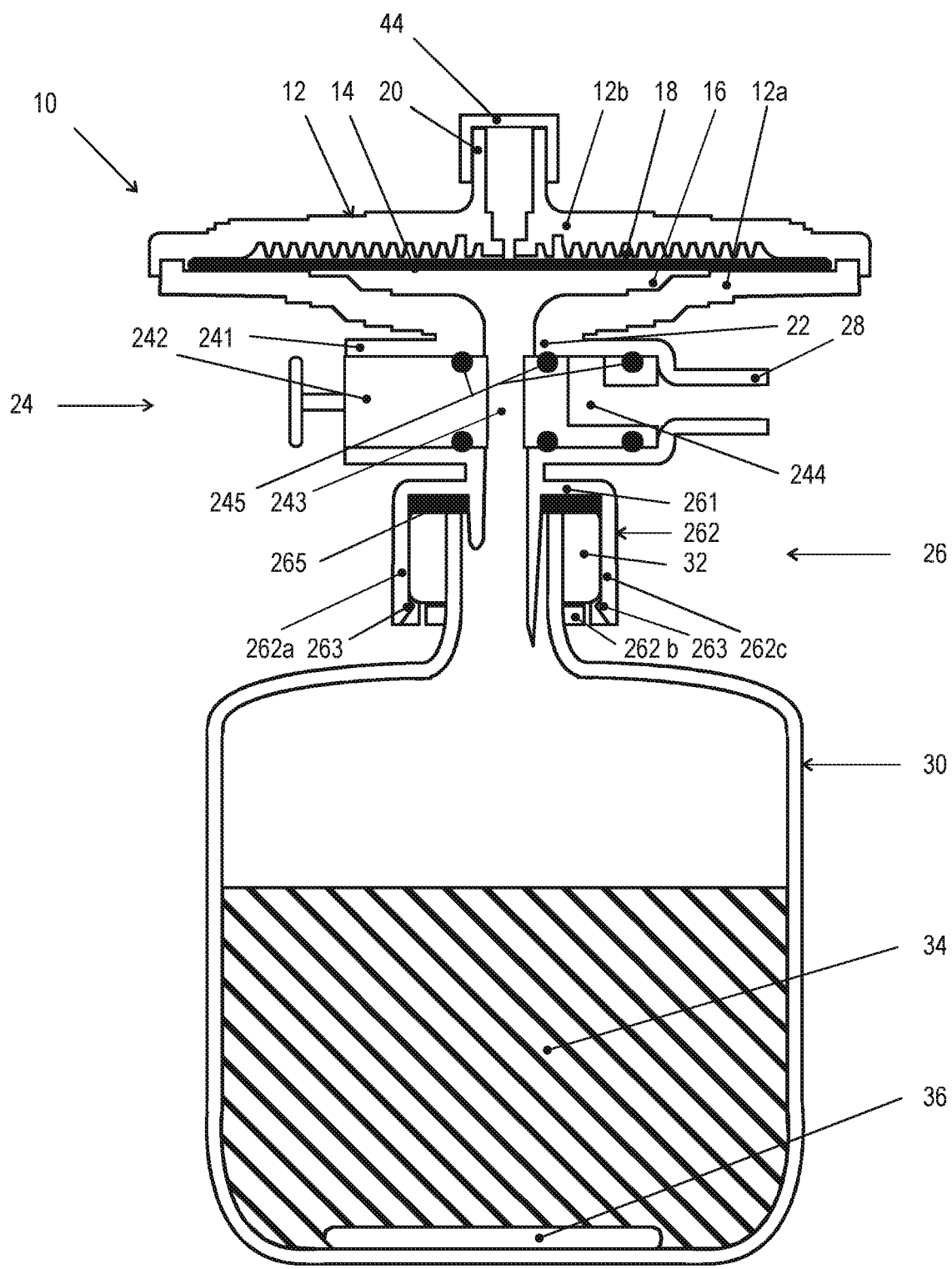
FIG. 4 shows the arrangement in FIG. 3 after switching of the valve position.

Then, possibly after one or more optional cleaning and/or flushing steps, as can be seen in FIG. 4, the test liquid reservoir and the collecting container are uncoupled. The outlet connecting piece 20 is preferably closed off by a closure cap 44. Explicit closure of the second connector 28 of the inlet connecting piece 22 is not required. Rather, said connector is closed through switching of the slide valve 24; at the same time, the connection between the culture medium bottle 30 and the inlet chamber 16 is opened.

Figure 5:
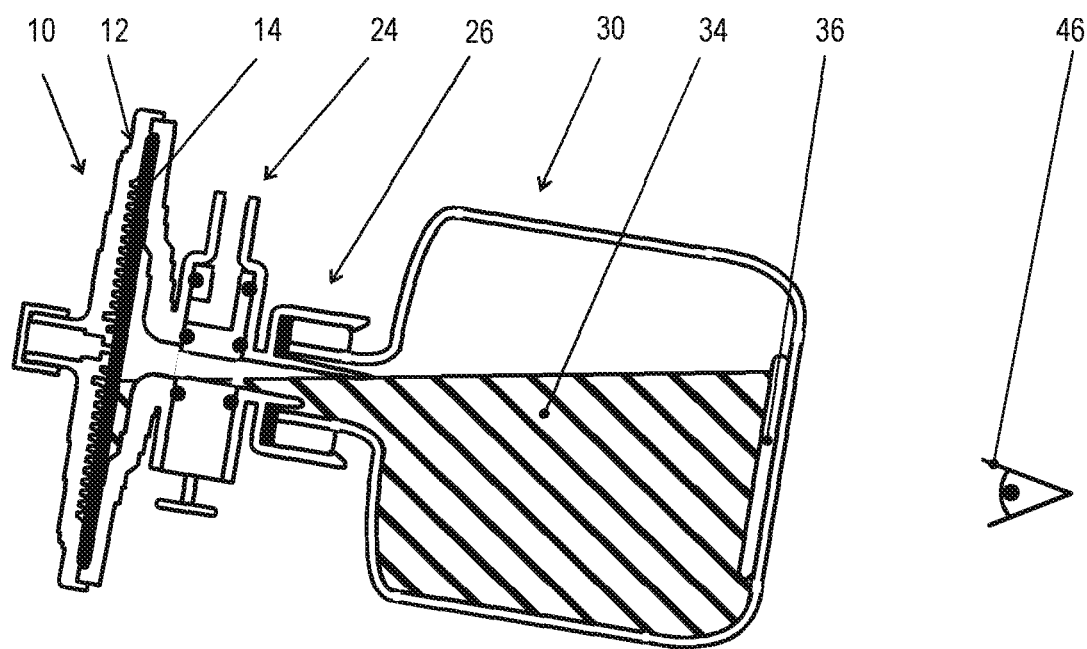
FIG. 5 shows the arrangement in FIG. 4 during the incubation step.
Figure 5:
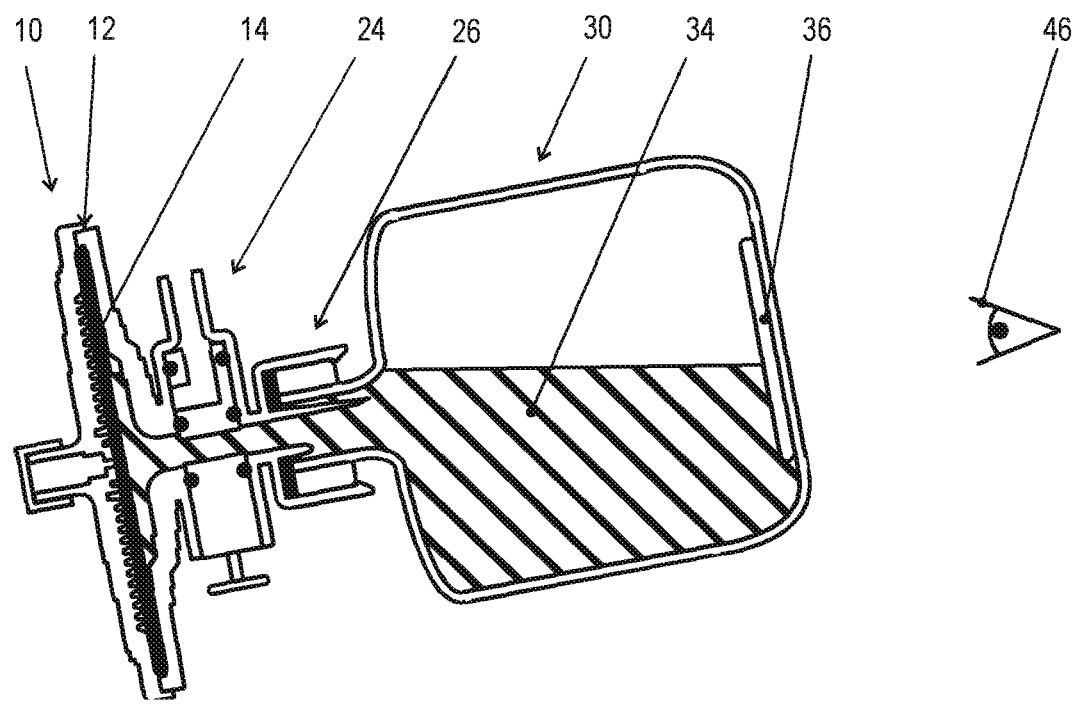

Tilting of the entire arrangement leads, as illustrated in FIG. 5, to the culture medium flowing through the first connector 26 of the inlet connecting piece 22 into the inlet chamber 16 and wetting the membrane filter 14. Also, at the same time, the microorganism activity sensor 36 remains wetted by the culture medium 34. It is preferable for the arrangement to be rocked periodically, as indicated in FIG. 5, and/or rotated about its central axis since the exchange of liquid is realized swiftly and permanent wetting of the membrane filter 14 and the microorganism activity sensor 36 is ensured.

The incubation is preferably realized in an incubation cabinet which ensures a suitable temperature for growth of the microorganisms on the membrane filter 14. The microorganism activity sensor 36 is in this case continuously, regularly or sporadically read, as indicated by the monitoring symbol 46 in FIG. 5.

Figure 6:
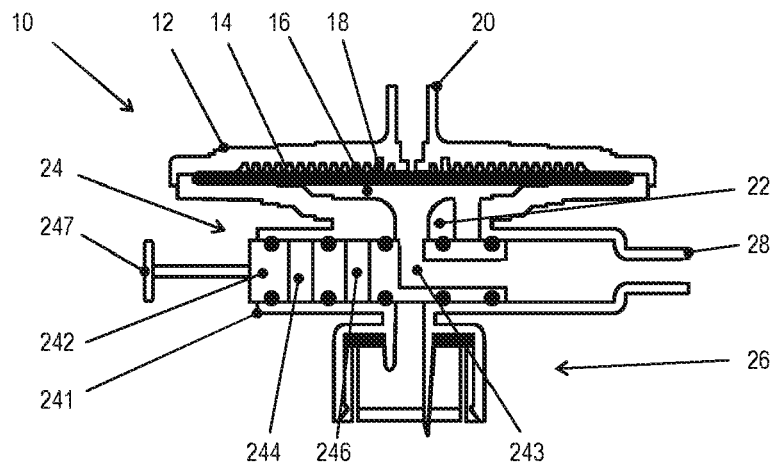
FIG. 6 shows a sectional illustration of an alternative embodiment of the filter module according to the invention in a first valve position.
Figure 7:
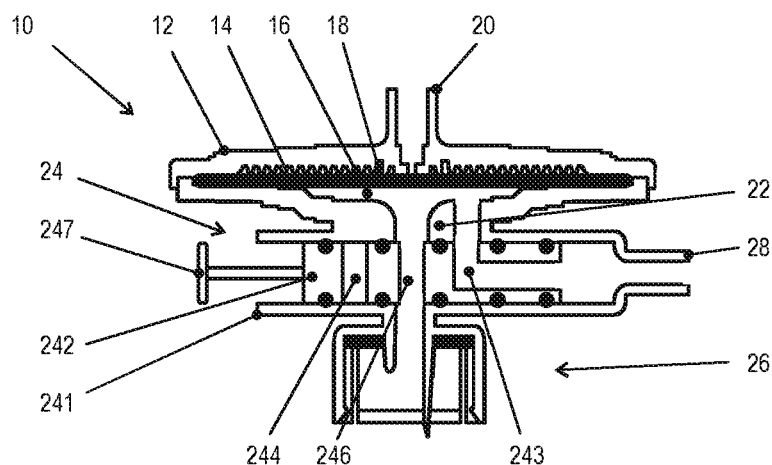
FIG. 7 shows a sectional illustration of the filter module in FIG. 6 in a second valve position.
Figure 8:
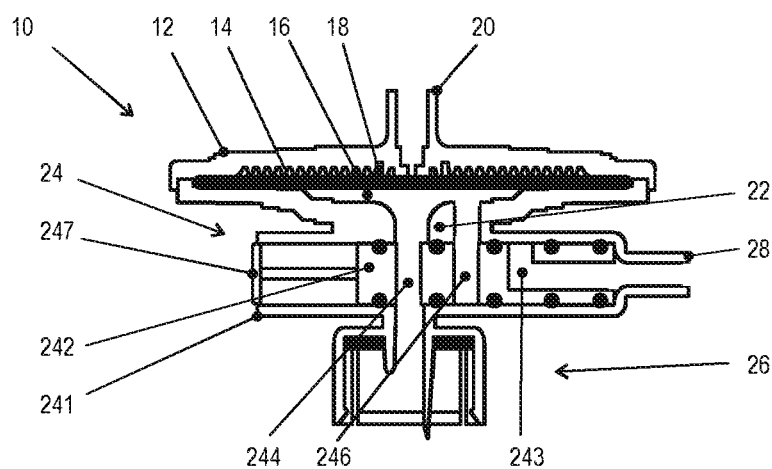
FIG. 8 shows a sectional illustration of the filter module in FIG. 6 in a third valve position.

FIGS. 6 to 8 show an alternative embodiment of a filter module 10 according to the invention, the slide valve 24 of which permits three different positions. For this purpose, the valve 24 has three valve channels 243, 244, 246. The valve position shown in FIG. 6 corresponds functionally to the valve position in FIG. 2 or in FIG. 3, that is to say only the second connector 28 is connected to the inlet chamber 16. As explained in the context of FIG. 3, the filtration step is carried out with this valve position. The valve position shown in FIG. 8 corresponds functionally to the valve position in FIG. 1 or FIG. 4, that is to say only the first connector 26 is connected to the inlet chamber 16. As explained in the context of FIG. 4, the incubation step is carried out with this valve position.

FIG. 7 shows an additional valve position, which is made possible by the additional, third valve channel 246. In this position, both the first connector 26 and the second connector 28 are connected—albeit via different flow paths—to the inlet chamber 16. It is consequently possible to pump culture medium from an external culture medium reservoir (not illustrated) into the culture medium bottle 30 via the inlet chamber. If this step is carried out following the filtration step and prior to the incubation step, it can be used to flush away microorganisms accumulated on the membrane filter 14 and to transport these into the culture medium bottle 30. This facilitates, during the subsequent incubation, growth of the microorganisms from the inlet chamber 16 through into the culture medium bottle and to the microorganism activity sensor 36. Said position can also be used for equalization of pressure between the culture medium bottle 30 and the surroundings (represented by the external culture medium reservoir). Finally, any dead volume in the system is eliminated. A reversed flow of culture medium from the culture medium bottle 30 into an external waste reservoir is also possible.

In the embodiment shown in FIGS. 6 to 8, the valve piston 242, in particular the actuation element 247 thereof, is dimensioned relative to the valve housing 241 such that, in the incubation position (FIG. 8), the valve piston actuation element 247 can latch to the valve housing 241, so that the transfer of the valve 24 into its incubation position is irreversible.

The embodiments discussed in the specific description and shown in the figures represent merely illustrative exemplary embodiments of the present invention. In the light of the disclosure here, a person skilled in the art is offered a broad spectrum of possible variants. In particular, in the detection method according to the invention, it is possible for multiple filter modules according to the invention to be used in a parallel manner and, if appropriate, coupled to different culture medium bottles, for example for aerobic microorganisms and for anaerobic microorganisms. Both isolated sterile filter modules and filter modules already coupled to a culture medium bottle at the first connector and/or to a sterile tube system at the second connector can be assembled as mercantile units. Uncoupled connectors may in each case be closed off by a removable sterile cap, by removable sterile paper or by tear-off shrink wrap. In the case of pre-coupled units, in particular in embodiments with two detent positions, delivery with a mechanically, but not fluidically, connected coupling of filter module and culture medium bottle is possible. A sterile shrink film can be fitted snugly around the coupling point, said shrink film sealing off the coupling point with respect to the surroundings. Other known and unknown measures for preserving the sterility of the respective mercantile unit are of course also able to be used.

LIST OF REFERENCE SIGNS

10 Filter module
12 Housing
12a Lower housing half
12b Upper housing half
14 Membrane filter
16 Inlet chamber
18 Outlet chamber
20 Filtrate outlet/outlet connecting piece
22 Inlet connecting piece
24 Slide valve
241 Valve housing
242 Valve piston
243 First valve channel
244 Second valve channel
245 Seal
246 Third valve channel
247 Valve piston actuation element
26 First connector
261 Cover
262 Collar
262a, b, c Collar segments
263 Detent projection
264 Cannula
265 Flat seal
28 Second connector
30 Culture medium bottle
32 Mouth thickening
34 Culture medium
36 Microorganism activity sensor
38 Flow arrow
40 Tube connection
42 Tube connection
44 Closure cap
46 Monitoring symbol

What is claimed is:

1. A filter module comprising:
a housing which is subdivided by a membrane filter into an inlet chamber, which is connected to an inlet connecting piece arranged rigidly on the housing, and an outlet chamber, which has a filtrate outlet, and
a 3-way valve integrated into the inlet connecting piece,
wherein the inlet connecting piece has a first connector and a second connector, which are configured to connect fluidically and selectively to the inlet chamber with the 3-way valve, wherein the 3-way valve comprises a first entry, which is connected to the first connector, a second entry, which is connected to the second connector, and an exit, which is connected to the inlet chamber, and
wherein the first connector comprises an adapter configured to seal outwardly to a culture medium bottle through a coupling, which coupling provides a gravity-driven exchange of liquid with the first entry of the 3-way valve.

2. The filter module as claimed in claim 1,
wherein the first connector and the second connector are each configured to connect individually fluidically to the inlet chamber.

3. The filter module as claimed in claim 2,
wherein the first connector and the second connector are configured to connect jointly fluidically, via mutually differing flow paths, to the inlet chamber.

4. The filter module as claimed in claim 1,
wherein the adapter comprises a central cannula and a collar which engages coaxially around the central cannula.

5. The filter module as claimed in claim 4,
wherein the collar is subdivided into at least two collar segments, which circumferentially adjoin one another and which are configured to pivot elastically relative to one another about respectively single tangential pivot axes.

6. The filter module as claimed in claim 5,
wherein the collar comprises radially inwardly projecting detent projections.

7. The filter module as claimed in claim 4,
wherein the collar comprises an internal thread.

8. The filter module as claimed in claim 1,
wherein the 3-way valve is a slide valve.

9. The filter module as claimed in claim 1,
wherein the 3-way valve is configured to switch irreversibly into a final switching position which connects the first connector to the inlet chamber from a preceding switching position which connects the second connector to the inlet chamber.

10. The filter module as claimed in claim 1,
wherein the first connector of the inlet connecting piece is oriented perpendicular to the membrane filter, and the second connector of the inlet connecting piece is oriented parallel to the membrane filter.

11. A method for detecting microorganisms in a test liquid, comprising:
a) providing a filter module as claimed in claim 1, wherein only the second connector, in a corresponding switching position of the 3-way valve, is connected to the inlet chamber,
b) coupling on the culture medium bottle via the adapter, wherein the culture medium bottle contains culture medium and an integrated microorganism activity sensor,
c) connecting the second connector to a test liquid reservoir,
d) pumping test liquid from the test liquid reservoir through the filter module,
e) switching the 3-way valve such that only the first connector is connected to the inlet chamber,
f) orienting the filter module and the coupled-on culture medium bottle such that both the membrane filter and the microorganism activity sensor are wetted by the culture medium, and
g) monitoring the microorganism activity sensor.

12. The method according to claim 11, further comprising, between the steps d and e:
d1) switching the 3-way valve such that the first connector and the second connector are jointly connected, via mutually differing flow paths, to the inlet chamber, and
d2) pumping the culture medium from an external culture medium reservoir, connected to the second connector, through the inlet chamber into the coupled-on culture medium bottle.

13. The method according to claim 11, further comprising, between the steps d and e:
d1) switching the 3-way valve such that the first connector and the second connector are jointly connected, via mutually differing flow paths, to the inlet chamber, and
d2) pumping the culture medium from the coupled-on culture medium bottle into a waste reservoir connected to the second connector.

* * * * *